(12) United States Patent
Berndt

(10) Patent No.: US 6,633,368 B2
(45) Date of Patent: Oct. 14, 2003

(54) METHOD FOR DETERMINING THE VOLUME OF SINGLE RED BLOOD CELLS

(75) Inventor: Klaus W. Berndt, Timonium, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 32 days.

(21) Appl. No.: 09/753,205

(22) Filed: Jan. 2, 2001

(65) Prior Publication Data

US 2002/0126272 A1 Sep. 12, 2002

(51) Int. Cl.[7] .................. G01N 33/48; G01N 15/02; G01N 21/64; G01N 21/03; G01B 11/22
(52) U.S. Cl. .................. 356/39; 356/627; 356/335; 422/82.08; 436/165
(58) Field of Search .................. 356/39, 317, 627, 356/335; 422/82.05, 82.08; 436/164, 165; 250/458.1, 459.1, 461.2

(56) References Cited

U.S. PATENT DOCUMENTS

| | | | | |
|---|---|---|---|---|
| 5,427,959 A | * | 6/1995 | Nishimura et al. | ......... 356/244 |
| 5,563,070 A | * | 10/1996 | Yamamoto et al. | ............ 435/2 |
| 5,948,686 A | * | 9/1999 | Wardlaw | ........................ 435/2 |
| 6,127,184 A | * | 10/2000 | Wardlaw | .................... 356/244 |
| 6,235,536 B1 | * | 5/2001 | Wardlaw | .................... 356/244 |

* cited by examiner

Primary Examiner—Zandra V. Smith
Assistant Examiner—Gordon J Stock, Jr.
(74) Attorney, Agent, or Firm—Bruce S. Weintraub

(57) ABSTRACT

The invention discloses a method for determining the volume of single red blood cells or other particles that are suspended in liquids. The sample is disposed into an optical cuvette suitable for microscopic analysis. A fluorescent dye is added that does not leak into the cells, and that is able to absorb excitation light and emit fluorescence light at wavelengths that are only weakly absorbed by the cells. The cell volume is determined using fluorescence intensity values measured (i) in a first area comprising a single cell, (ii) in a second area close to that cell, and (iii) in said second area, after changing the cuvette thickness by a known amount.

52 Claims, 7 Drawing Sheets

METHOD FOR DETERMINING THE VOLUME OF SINGLE RED BLOOD CELLS

FIELD OF THE INVENTION

The present invention relates to the field of quantitative microspectroscopy, and in particular to a method for determining the volume of single red blood cells.

BACKGROUND OF THE INVENTION

Determining the volume of single red blood cells and, based on this measurement, calculating the Mean Cell Volume ("MCV") and the Red Cell Distribution Width ("RDW") is of clinical interest. Usually, systems based on electrical impedance measurement (Coulter Counter) or based on light scattering (Flow Cytometer) are employed (see. e.g., J. B. Henry, "Clinical diagnosis and management by laboratory methods", W. B. Saunders Company, Philadelphia, 1996, pp. 548 ff. or D. H. Tycko, M. H. Metz, E. A. Epstein, A. Grinbaum, "Flow-cytometric light scattering measurement of red blood cell volume and hemoglobin concentration", Applied Optics 24 (1985), 1355–1365). Impedance counters are complex and expensive instruments that require very careful adjustment and control of instrument and sample parameters. A major disadvantage of flow cytometers is the fact that the parameters of light scattering depend not only on cell volume, but also on cell shape.

In 1983, Gray, Hoffman and Hansen proposed a new optical method for determining the volume of cells in a flow cytometer (M. L. Gray, R. A. Hoffman, W. P. Hansen, "A new method for cell volume measurement based on volume exclusion of a fluorescent dye", Cytometry 3 (1983), 428–432). In this method, the cells are suspended in a fluorescent dye, which is unable to penetrate the cell membrane. The level of fluorescence which is produced when a narrow stream of the cell suspension is excited by a focused laser beam will remain constant until a cell arrives in the illuminated region thereby causing a decrease in fluorescence intensity which is directly proportional to the cell's volume. In a flow cytometer, a single cell is passing through the laser-illuminated spot within approximately 10 s. Due to this short data acquisition time interval, the electronic detection bandwidth has to be relatively large, which results in a poor signal-to-noise ratio and in a low precision for the volume determination.

The available data acquisition time can be significantly increased by suspending the cells in a stationary sample and applying digital imaging fluorescence microscopy (see P. L. Becker, F. S. Fay, "Cell-volume measurement using the digital imaging fluorescence microscope", Biophysical Journal 49 (1986), A465). In the digital fluorescence microscopy approach, a calibration procedure is required in order to determine the cell volume. Recktenwald and co-workers have introduced a method where the calibration is performed by means of optical transparent and non-fluorescent microspheres that are suspended together with the cells (D. Recktenwald, J. Phi-Wilson, B. Verwer, "Fluorescence quantitation using digital microscopy", Journal Physical Chemistry 97 (1993), 2868–2870). The volume of individual spheres is determined by measuring their projection area under the microscope and transforming this number into a volume, assuming an ideal spherical shape. The decrease in fluorescence intensity as a result of the spheres' volume that is being excluded from emitting fluorescence is used as the required calibration parameter. The advantage of this approach is given by the fact that the calibrating particles are located within the sample itself. In other words, a calibration is performed on the very same sample container, and no extra calibration sample is required.

The use of calibration spheres within a cell suspension is not without problems. First, the introduction of the spheres represents an additional step in the workflow. In systems that are designed for high throughput, this additional step would represent a disadvantage. Secondly, Recktenwald and co-workers observed a tendency of the fluorescent dye molecules to settle down on the sphere's surface, which causes an error. Third, if the optical index of refraction of the spheres does not match well with the liquid's index, then refraction-based artifacts in the measured fluorescence intensity occur at the edges of the spheres. And, finally, the use of microspheres can represent a problem, if e.g. a thin sample thickness in the order of a few micrometers or less is needed.

In order to overcome the problems in the prior art, it has been suggested (K. W. Berndt, "Method for determining the volume of particles suspended in liquids", P-3875, 1997), to design a sample container for the cell suspension that has different optical path lengths in different areas. Preferably, a step-like profile in one of the container windows is employed. In the immediate neighborhood of such step, the change in optical path length is well known, and independent of any possible tilting of the sample container relative to the microscope's optical Z-axis. The change in intensity due to the well-known step width allows for calibrating the volume determination procedure. The disadvantage of this approach is given by the fact that no cells are allowed at the step, which in practice is not always guaranteed. Also, the production of sample containers equipped with very precise calibration steps in one of the container windows is likely to being costly.

In view of the disadvantages and problems in the prior art as described above, there exists a need for a simple and reliable method for determining the volume of single red blood cells suspended in a liquid.

SUMMARY OF THE INVENTION

It is an objective of the present invention to provide a method for determining the volume of single red blood cells or other particles that are suspended in liquids.

According to the present invention, and for the case of red blood cells, the above objective is achieved by depositing a liquid sample that contains suspended red blood cells into an optical cuvette having at least one transparent window, by adding and evenly distributing a fluorescent dye into the liquid that does not leak into the red blood cells, and that is able to absorb excitation light at wavelengths that are only weakly absorbed by the red blood cells, and is able to emit fluorescence light at wavelengths that are only weakly absorbed by the red blood cells; by illuminating the sample at a wavelength that is absorbed by the fluorescent dye, but only weakly absorbed by the red blood cells, by measuring the reemerging fluorescence intensity in an area that contains no red blood cells, by changing the cuvette thickness in that area by a well-defined amount and measuring the reemerging fluorescence intensity in the same area again, by measuring the reemerging fluorescence intensity in an area where a red blood cell resides, by measuring the reemerging fluorescence intensity in an area close to that same red blood cell, and by calculating the volume of the red blood cell based on these fluorescence intensity values and the known change in cuvette thickness.

BRIEF DESCRIPTION OF THE DRAWINGS

In FIG. 6, we assume a cylindrical cell of area, $A_{RBC}$, and of height, $h_{RBC}$.

DETAILED DESCRIPTION OF THE INVENTION

According to the method of the present invention, a liquid sample that contains suspended red blood cells is deposited into an optical cuvette having at least one transparent window. Preferably, the cuvette is relatively thin and suitable to be positioned onto the sample stage of a fluorescence microscope. For example, the cuvette can be built by placing a flexible #1 coverslip of 24 mm×50 mm size onto spacers that are residing on a common microscope slide of 25 mm×75 mm size. The preferred height of the spacers is approximately 200 m. By pressing onto the flexible coverslip, thickness values in the center region of the cuvette between less than 1 m and 200 m can be achieved. An opticabuvette is any container that is able to hold a liquid sample within its interior space and that has at least one transparent window, allowing for fluorescence measurement. It would also be within the spirit of the invention to use a cuvette with two windows on opposite sides. It would still be within the spirit of the invention to use a container with one transparent window on one side and a mirror on the other side. In this case, excitation light would enter the container through said one transparent window, would cross the liquid sample twice, and fluorescence light would exit the container through the same window. The one window would function as both entrance window and exit window. The invention is not limited to containers for microscopic analysis, but is applicable also for containers of larger size that are interrogated on optical systems other than microscopes.

A fluorescent dye is added to, and evenly distributed within the liquid sample. The dye is selected so that it does not leak into the red blood cells. Also, it should absorb excitation light and emit fluorescence light within a spectral region where the absorption within the red blood cells is only weak. Since hemoglobin is the dominant absorber in red blood cells, the excitation wavelength has to be longer than 600 nm. One good candidate dye is TO-PRO-3 (sold, for example, by Molecular Probes, Inc., Eugene, Oreg.), that can be excited within a wavelength range around to 640 nm, and is emiiting fluorescence above 640 nm. Another possible dye would be TO-PRO-5 (sold by Molecular Probes, Inc.), which also does not penetrate into the red blood cells, can be excited around 750 nm, and is emitting fluorescence above 750 nm. It is apparent to one skilled in the art that the invention is not limited to the two dyes mentioned above. Many other dyes are available that fulfill the spectral conditions for measurements on red blood cells, and even more dyes are available that fulfill the spectral conditions for other particles. It would of course also still be within the spirit of the present invention to add and evenly distribute the fluorescent dye within the liquid sample prior to disposing the sample into the container.

Figure 1:
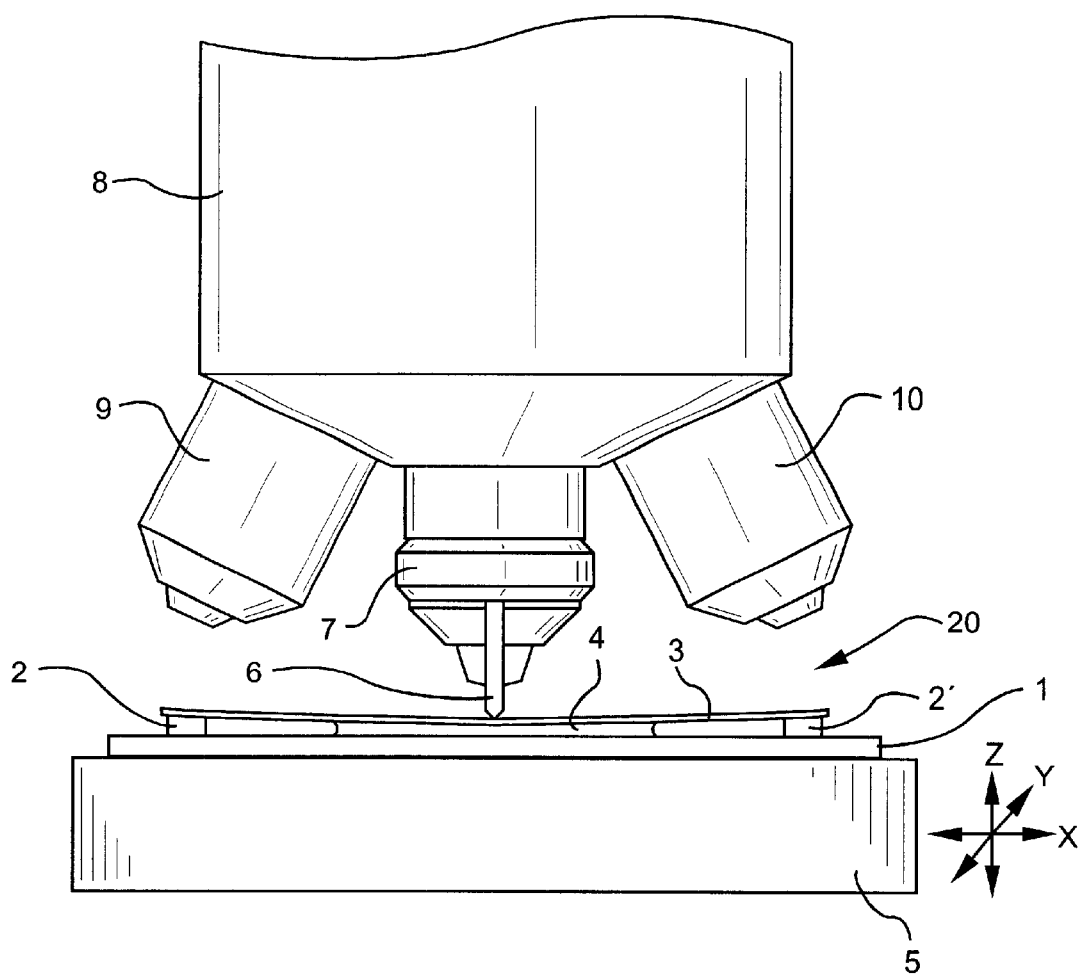
FIG. 1 depicts a measuring set-up with an optical cuvette having one flexible window, and containing a liquid sample comprising suspended red blood cells.
Figure 2:
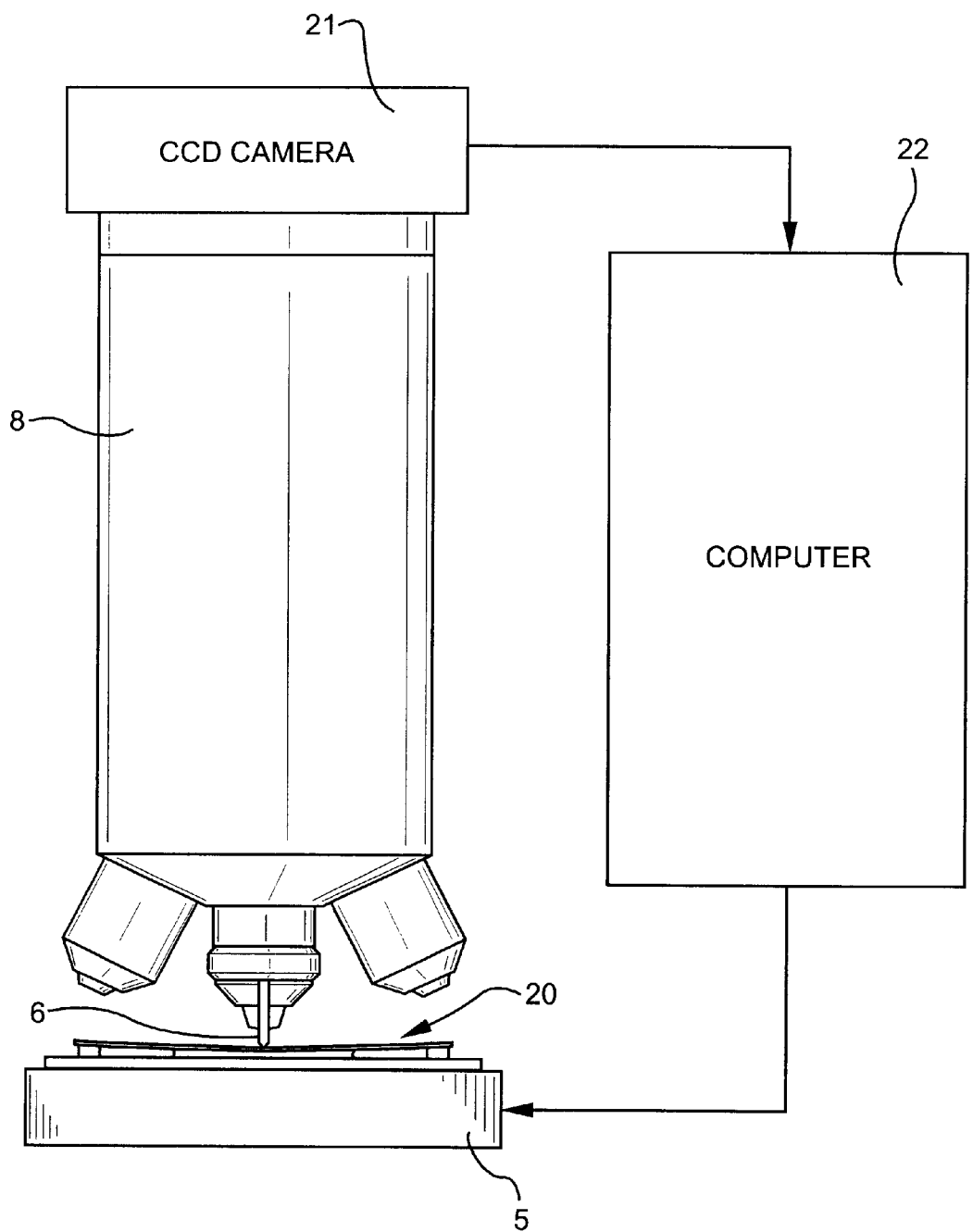
FIG. 2 illustrates a complete set-up comprising sample container, XYZ-stage, fluorescence microscope, CCD camera, and computer.

FIG. 1 depicts a measuring set-up with an optical cuvette (20) having one flexible window (3), and containing a liquid sample (4) comprising suspended red blood cells. The cuvette is built by using a common microscope slide (1) that carries spacers (2, 2') to hold a flexible cover slip (3). The suspension of red blood cells in a liquid such as blood plasma (4) is contained between slide (1) and cover slip (3). The optical cuvette is positioned on an XYZ-stage (5) of a common fluorescence microscope (8) having interchangeable objective lenses (7, 9, and 10). As shown in FIG. 2, microscope (8) is equipped with a CCD camera (21) that is connected to a computer (22) for storing data and performing image-processing procedures. Computer (22) is also connected to XYZ-stage (5) to move cuvette (20) as needed.

Figure 3:
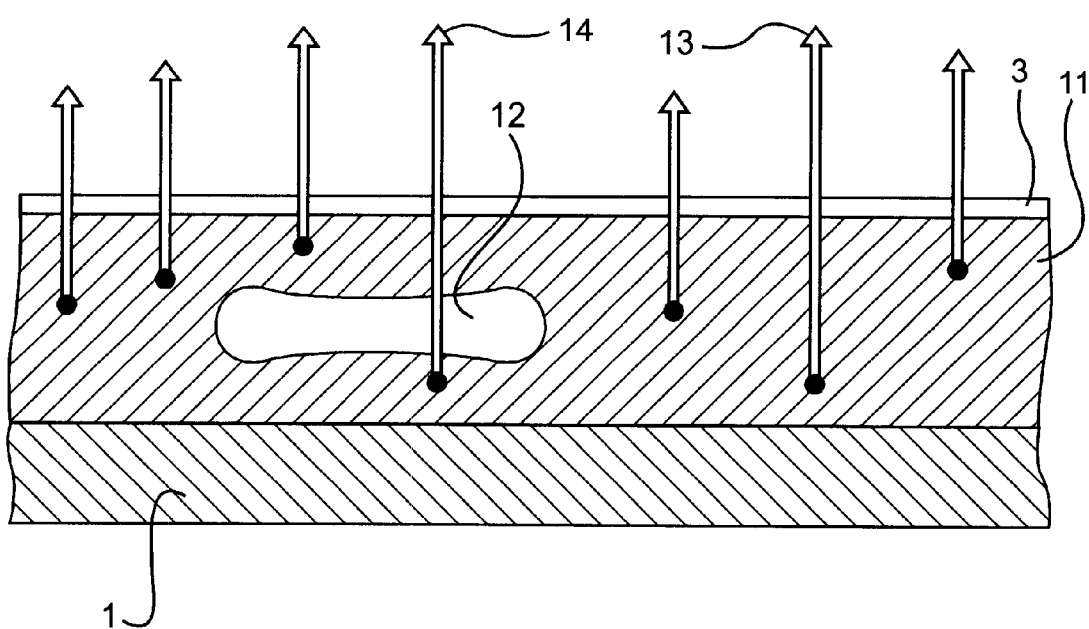
FIG. 3 shows schematically an optical cuvette with a region containing a weakly absorbing red blood cell, and another region containing no cells. The arrows illustrate fluorescence photons reemerging from the liquid suspension.

FIG. 3 illustrates a situation according to the present invention where the liquid sample (11) containing a fluorescent dye is illuminated with excitation light (not shown), and is re-emitting fluorescence photons (13, 14). As indicated in FIG. 3, the optical absorption within a red blood cell (12) is so weak that dye molecules "behind" a red cell can be excited, and fluorescence photons (14) emitted by those molecules can penetrate the cells (12) on their way towards the CCD camera.

In operation, cuvette (20) is moved upwards by means of stage (5) until flexible window (3) comes into physical contact with a fixed plunger (6) that is mounted onto objective lens (7) in such a way that the focal plane of microscope (8) lies within liquid sample (4) if flexible window (3) is touching plunger (6). If necessary, cuvette (20) is being moved in X- and Y-directions until a sample area containing no red blood cells comes into the field of view. If the sample is whole blood, then it is appropriate to use a cuvette thickness in the range of 2 $\mu$m to 30 $\mu$m in order to have areas containing no red blood cells readily available. For diluted blood samples, thicker cuvettes can be used.

Figure 4:
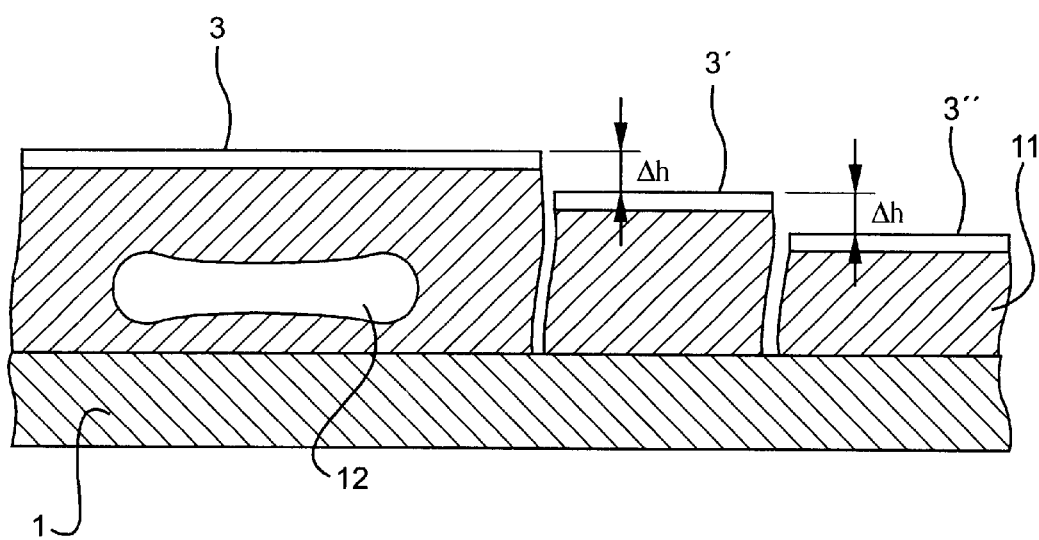
FIG. 4 shows schematically an optical cuvette with a region containing a weakly absorbing red blood cell, and another region containing no cells, whereby the flexible cuvette window has been moved twice by step widths of h.
Figure 5:
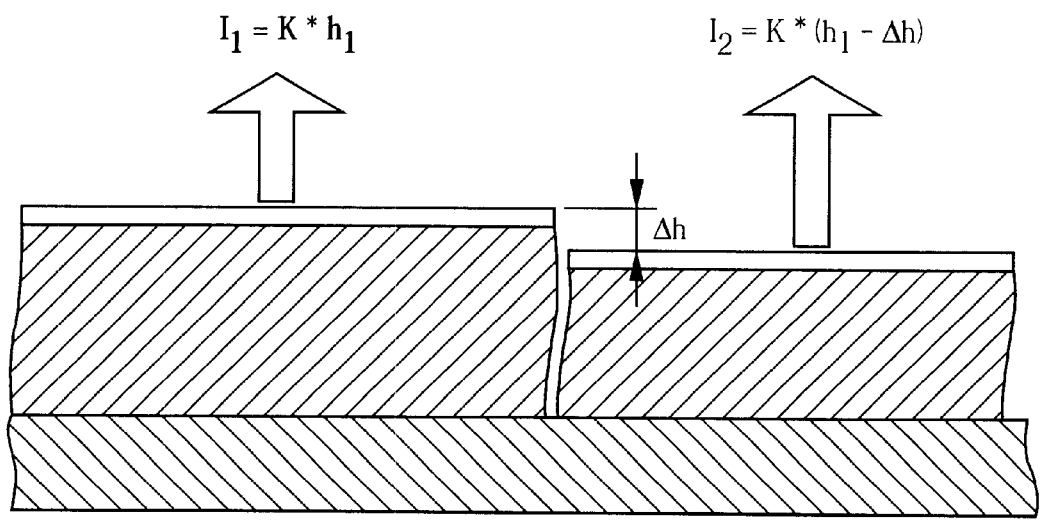
FIG. 5 illustrates the calibration procedure, where the cuvette thickness in an area that contains no red blood cells is changed by a well-defined amount, h, and the reemerging fluorescence intensities, $I_1$ and $I_2$, are measured prior to and after changing the thickness. In this example, the cuvette thickness has been reduced.

Once an area containing no red blood cells has been found, the sample is illuminated with excitation light of appropriate wavelength from within the fluorescence microscope, and the fluorescence intensity, $I_1$, in that area is measured by means of CCD camera (21), and the result stored in computer (22). In a next step, cuvette (20) is moved further upwards by means of stage (5) by a small, but precisely known distance, $\Delta h$. Moving cuvette (20) upward against fixed plunger (6) results in a reduction in the optical path length within the cuvette by an amount identical to h. When cuvette (20) has been moved, a new fluorescence intensity, $I_2$, in the same area is measured, and the result stored in computer (22). The new fluorescence intensity, $I_2$, has a lower value than the first intensity, $I_1$, because a smaller sample volume is emitting fluorescence photons. This is illustrated in FIG. 4 and FIG. 5.

The two fluorescence intensity values, $I_1$ and $I_2$, together with the change in optical path length, h, can be used to calibrate the set-up by calculating a ratio "change in fluorescence/change in path length". Referring to FIG. 5, this calibration can be explained as follows.

Assuming that the liquid sample is evenly illuminated by excitation light, the first fluorescence intensity, $I_1$, is given by $$I_1 = K * h_1 + I_{AF} \quad (1)$$

where the quantity K contains such parameters as excitation intensity, fluorescence quantum yield, fluorophore concentration, fluorophore absorption coefficient, transfer function of the spectral excitation and emission windows, optical transfer function of the microscope, photo detection sensitivity. K is the one quantity that has to be calibrated. For the following discussion, we can assume that K is constant and independent of the X- and Y-positions used. The quantity $h_1$ is the optical path length (or thickness) of cuvette (20) at the area that is measured. $I_{AF}$ represents a possible autofluorescence contribution from the cuvette material.

The fluorescence intensity, $I_2$, which is measured after changing the cuvette thickness by an amount of h is given by $$I_2 = K * (h_1 - \Delta h) + I_{AF} \quad (2)$$

By subtracting equation (2) from equation (1), we obtain an expression for K, which represents our calibration quantity:

$$K = \frac{I_1 - I_2}{\Delta h}. \quad (3)$$

Equation (3) indicates that there is no need for knowing the absolute cuvette thickness, $h_1$, and that any autofluorescence contribution, $I_{AF}$, is canceled out.

Figure 7:
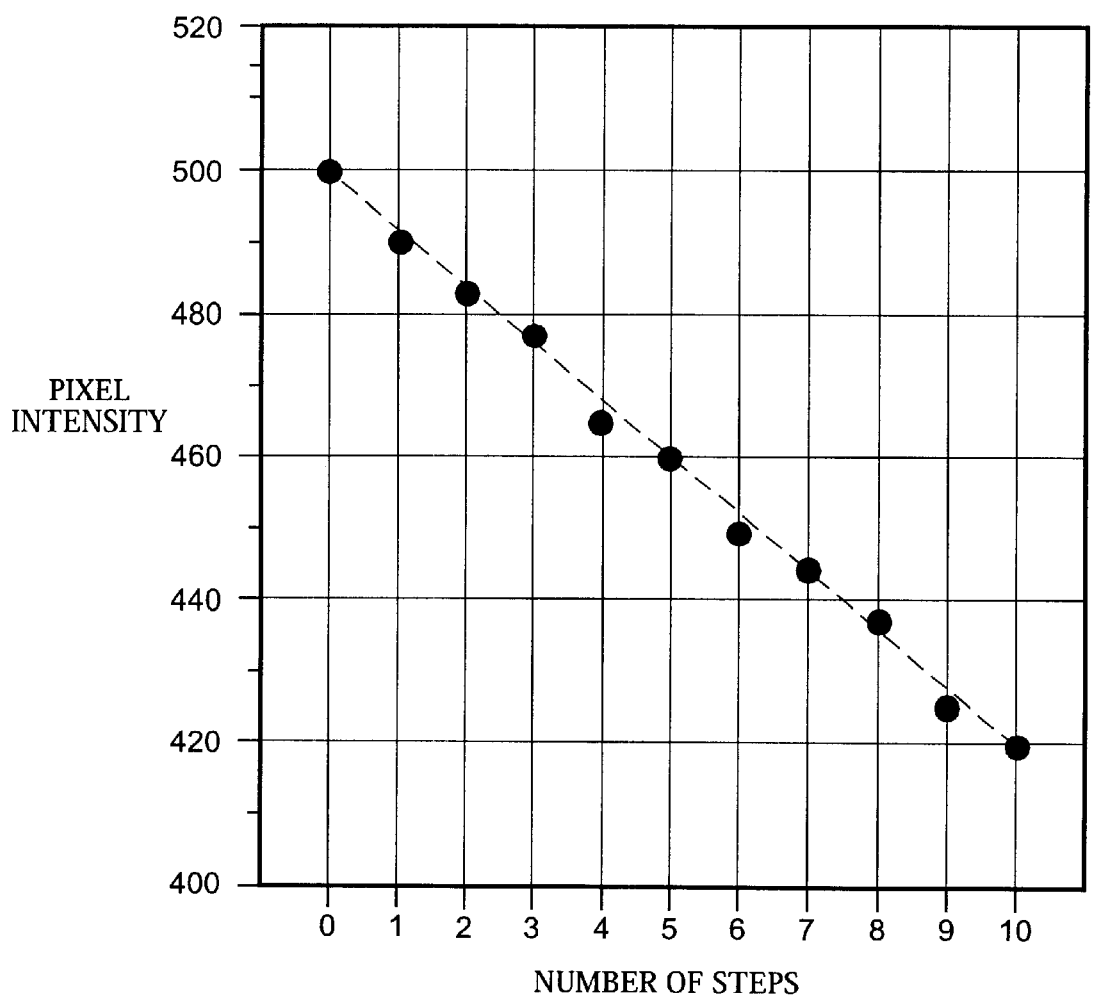
FIG. 7 shows a typical plot of reemerging fluorescence intensity, expressed as pixel intensity of the CCD camera, if a cuvette thickness of approximately 10 m is reduced in ten steps of 0.2 m each, down to approximately 8 m.

In order to enhance the calibration precision, it is possible to employ more than one change, $\Delta h$, in cuvette thickness. This is indicated in FIG. 4, wherein liquid sample (11) contains a red blood cell (12), and flexible window (3) is moved successively by a first step $\Delta h$ to a new position (3'), and by a second step $\Delta h$ to still another position (3"). FIG. 7 shows a typical plot of reemerging fluorescence intensity, expressed as pixel intensity of the CCD camera, if a cuvette thickness of approximately 10 $\mu$m is reduced in ten steps of 0.2 $\mu$m each, down to approximately 8 $\mu$m. From the plot in FIG. 7, a calibration value K=39.993 $\mu$m$^{-1}$ is obtained.

Figure 6:
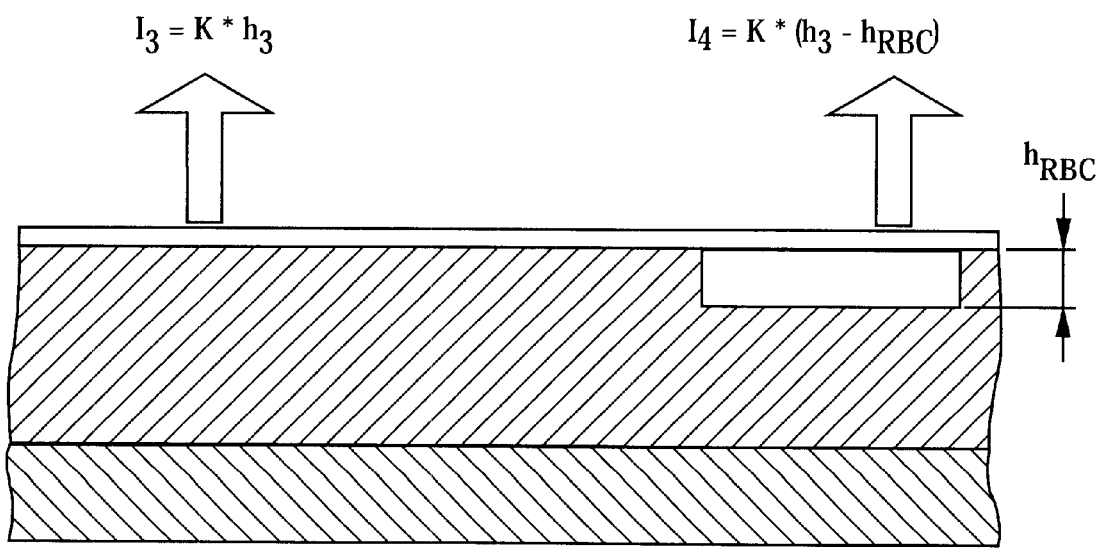
FIG. 6 illustrates the measuring procedure, where the reemerging fluorescence intensities, $I_3$ and $I_4$, are measured in an area where a red blood cell resides, and in an area close to that same cell.

After performing a calibration as outlined above, in the method according to the present invention, the volume of a single red blood cell is determined in the following way:

In a first step, and referring to FIG. 6, the reemerging fluorescence intensity, $I_4$, is measured in an area where a red blood cell resides. For the moment, we assume that the red blood cell has a cylindrical shape of area $A_{RBC}$, and of height $h_{RBC}$. In a second step, the reemerging fluorescence intensity, $I_3$, is measured in an area close to that same red blood cell. Considering that $I_4$ is given by $$I_4 = K * (h_3 - h_{RBC}) + I_{AF} \quad (4)$$

and $I_3$ is given by $$I_3 = K * h_3 + I_{AF} \quad (5)$$

we obtain $$I_3 - I_4 = K * h_{RBC} \quad (6)$$

which contains our calibration quantity K, as shown in equation (3). Equation (6) can be re-written in the form $$V_{RBC} = A_{RBC} * h_{RBC} = A_{RBC} * \frac{I_3 - I_4}{K}, \quad (7)$$

which represents the expression for the volume, $V_{RBC}$, of a single cylindrical red blood cell.

It should be emphasized that the method according to the present invention is based on differential measurements regarding the thickness of the cuvette as well as the reemerging fluorescence intensities. In other words, there is no need to know the absolute thickness of the cuvette. Moreover, there is no need to know the excitation intensity, which is injected into the cuvette. Combining equation (7) for the cell volume with equation (3) for the calibration quantity K results in $$V_{RBC} = A_{RBC} * \Delta h * \frac{I_3 - I_4}{I_1 - I_2}. \quad (8)$$

Equation (8) shows that any long-term drift in the instrumental parameters are canceled out. This results from the fact that the volume of a red blood cell, $V_{RBC}$, is calculated from a ratio of photocurrents. In other words, if the calibration procedure is executed closely in time with the measurement, then the method according to the present invention is very robust. This condition will always be fulfilled, since the calibration procedure is performed on the very same sample that is being measured.

So far, it has been assumed that the red blood cell has a cylindrical shape. It can be shown that the shape of the red blood cell can be irregular and that the Z-position of the cell within the cuvette has no impact on the calculated cell volume. The volume of a cell, $V_{RBC}$, is related to the spatially dependent cell height, $h_{RBC}(,)$, via the equation $$V_{RBC} = \int h_{RBC}(\xi, \eta) d\xi d\eta, \quad (9)$$

where the quantities and represent the independent X- and Y-variables within the red blood cell. By combining equations (8) and (9), we obtain $$V_{RBC} = \frac{\Delta h}{I_1 - I_2} \int [I_3 - I_4(\xi, \eta)] d\xi d\eta. \quad (10)$$

The integration procedure shown in equation (10) has not to be performed exactly over the area occupied by a red blood cell. Instead, it could be performed over a somewhat larger area that includes the cell. Outside of the cell, $I_4(\xi,\eta)$ is identical to $I_3$; therefore $I_3 - I_4(\xi,\eta) = 0$. In other words, extending the integration over a larger area beyond the cell's perimeter would not result in additional contributions to the calculated cell volume. This aspect of the invention allows for the use of simple one-size one-shape integration areas for all individual cells that are studied. Consequently, the required calculations can be executed within a shorter time interval. It should be noted that it is assumed, as equation (10) implies, that the intensity $I_3$ near the cell is constant. While $I_4(\xi,\eta)$ is measured in practice as an intensity of single CCD pixels, $I_3$ can be determined with maximum precision as the sum of all pixel intensities over an area, divided by the number of pixels. In other words, $I_3$ is the average pixel intensity near the cell.

The method for determining the volume of single red blood cells according to the present invention can be applied to whole blood or to diluted blood samples. The present invention can also be applied to a whole cluster of red blood cells or other particles in a liquid suspension, and not only to individual particles or cells. It would also be within the spirit of the invention to apply this method to other particles suspended in liquids such as beads or other particles or cells, for example, prokaryotic, bacterial, eukaryotic, mammalian, tissue culture or human cells. It is also apparent to one skilled in the art that the present invention can also be applied to particles or cells in other liquid suspensions or samples or dilutions thereof, such other medical or biological samples including tissue cultures or other cells in culture, including bacterial cultures, and other body fluids such as blood, urine, sputum, saliva and lymph fluid.

Depending on the optical properties of a liquid sample, the method can also be applied in cuvettes of higher thickness. Using a flexible window is only one example for achieving a change in the thickness of the cuvette. It would also be possible to use a stiff window, but spacers made out of a flexible material such as rubber. Still another embodiment would be possible by utilizing a flexible cuvette wall instead of localized spacers. Also, the change in cuvette thickness can be achieved by leaving the main part of the cuvette fixed, and acting with a positive or negative force onto the window, so that the window is moving. Such positive or negative forces may even involve the use of pressure or vacuum.

As has been already mentioned above, the invention is not limited to optical microscopes. Any imaging system that allows measuring fluorescent light intensities in areas that contain a particle and in areas that do not contain a particle are suitable to practice the present invention. The imaging system may contain lenses, but may also use fiber-optic elements in so-called proximity configurations. In this case, a coherent fiber-optic bundle is arranged between a cuvette window and an imaging photodetector. Finally, it would still be within the spirit of the present invention to scan a beam of excitation light across the cuvette windows and to monitor the re-emitted fluorescence light with a non-imaging photodetector, while the thickness of the cuvette is changing.

It should be mentioned that the step of calibration, i.e. determining the quantity K, "change in fluorescence/change in volume" according to equation (3) can also be performed in close proximity to the particle under investigation. In this case, and referring to FIG. 4, one would measure first the fluorescence intensity in the neighborhood of a single particle. In a next step, the thickness of the optical cuvette in this area is being changed by an amount $\Delta h$, and a new fluorescence intensity is measured. In a third step, the fluorescence intensity in the area occupied by the particle is measured. While the first two steps provide the required calibration quantity K, the second and the third step provide the two fluorescence intensity values that are needed for the actual volume measurement. This second procedure according to the present invention has the advantage that three instead of four steps are required. The first procedure according to the present invention allows performing the calibration within a cuvette area of increased thickness, which would allow for a more precise calibration value due to the increased intensity levels. In practice, the user has to decide, based on the priorities at hand.

While the present invention is described herein in terms of certain preferred embodiments, those skilled in the art will recognize that various modifications and improvements may be made to the invention without departing from the scope thereof. Moreover, although individual features of one embodiment are not in other embodiments, it would be apparent that individual features of one embodiment may be combined with one or more features of another embodiment or features from a plurality of embodiments.

What is claimed is:

1. A method for determining the volume of particles in a liquid, the method comprising:

(a) obtaining a suspension of particles in a liquid;

(b) depositing said suspension into a container having at least one transparent window;

(c) adding a fluorescent dye to said suspension in said container that does not substantially leak into said particles, wherein said fluorescent dye is able to absorb excitation light at wavelengths that are only weakly absorbed by said particles and emit fluorescence light at wavelengths that are only weakly absorbed by said particles;

(d) illuminating said suspension with light, whereby the wavelength of said light is selected so that said light is being absorbed by said fluorescent dye but only weakly absorbed by said particles;

(e) measuring a first intensity of fluorescent light that reemerges from said suspension in a first area of said suspension, wherein said first area contains no particles;

(f) changing the thickness of said container in said first area by a known amount by pressing on said container from outside of said container and measuring a second intensity of fluorescent light that reemerges from said suspension in said first area;

(g) measuring a third intensity of fluorescent light that reemerges from said suspension in a second area of said suspension, wherein said second area contains at least one particle;

(h) measuring a fourth intensity of fluorescent light that reemerges from a third area of said suspension close to said at least one particle in said second area; and (i) determining the volume of said at least one particle based on said fluorescent light intensity values and said known change in thickness of said container.

2. A method for determining the volume of particles in a liquid, the method comprising:

(a) obtaining a suspension of particles in a liquid;

(b) adding a fluorescent dye to said suspension forming a mixture, wherein said fluorescent dye does not substantially leak into said particles and is able to absorb excitation light at wavelengths that are only weakly absorbed by said particles and emit fluorescence light at wavelengths that are only weakly absorbed by said particles;

(c) depositing said mixture into a container having at least one transparent window;

(d) illuminating said mixture with light, whereby the wavelength of said light is selected so that said light is being absorbed by said fluorescent dye but only weakly absorbed by said particles;

(e) measuring a first intensity of fluorescent light that reemerges from said mixture in a first area of said mixture, wherein said first area contains no particles;

(f) changing the thickness of said container in said first area by a known amount by pressing on said container from outside of said container and measuring a second intensity of fluorescent light that reemerges from said mixture in said first area;

(g) measuring a third intensity of fluorescent light that reemerges from said mixture in a second area of said mixture, wherein said second area contains at least one particle;

(h) measuring a fourth intensity of fluorescent light that reemerges from a third area of said mixture close to said at least one particle in said second area; and determining the volume of said at least one particle based on said fluorescent light intensity values and said known change in thickness of said container.

3. The method of claim 1 wherein the particle is a cell.
4. The method of claim 2 wherein the particle is a cell.
5. The method of claim 3 wherein the cell is a human cell.
6. The method of claim 4 wherein the cell is a human cell.
7. The method of claim 3 wherein the cell is a red blood cell.
8. The method of claim 4 wherein the cell is a red blood cell.
9. The method of claim 1 wherein the liquid is a biological or medical sample.
10. The method of claim 2 wherein the liquid is a biological or medical sample.
11. The method of claim 9 wherein the biological or medical sample comprises a body fluid.
12. The method of claim 10 wherein the biological or medical sample comprises a body fluid.
13. The method of claim 11 wherein the body fluid is selected from the group consisting of blood, urine, sputum, saliva and lymph fluid.
14. The method of claim 12 wherein the body fluid is selected from the group consisting of blood, urine, sputum, saliva and lymph fluid.
15. The method of claim 9 wherein the biological or medical sample comprises tissue culture cells.
16. The method of claim 10 wherein the biological or medical sample comprises tissue culture cells.
17. The method of claim 9 wherein the biological or medical sample comprises bacterial cells.
18. The method of claim 10 wherein the biological or medical sample comprises bacterial cells.
19. The method of claim 1 wherein the container is an optical cuvette.
20. The method of claim 2 wherein the container is an optical cuvette.
21. The method of claim 19 wherein the optical cuvette comprises at least one transparent window.
22. The method of claim 20 wherein the optical cuvette comprises at least one transparent window.
23. The method of claim 19 wherein the optical cuvette comprises a microscope slide and a cover slip.
24. The method of claim 20 wherein the optical cuvette comprises a microscope slide and a cover slip.
25. The method of claim 1 wherein the dye is selected from the group consisting of TO-PRO-3 and TO-PRO-5.
26. The method of claim 2 wherein the dye is selected from the group consisting of TO-PRO-3 and TO-PRO-5.
27. A method for determining the volume of particles in a liquid, the method comprising:
  (a) obtaining a suspension of particles in a liquid;
  (b) depositing said suspension into a container having at least one transparent window;
  (c) adding a fluorescent dye to said suspension in said container that does not substantially leak into said particles, wherein said fluorescent dye is able to absorb excitation light at wavelengths that are only weakly absorbed by said particles and emit fluorescence light at wavelengths that are only weakly absorbed by said particles;
  (d) illuminating said suspension with light, whereby the wavelength of said light is selected so that the light is being absorbed by said dye but only weakly absorbed by said particles;
  (e) measuring a first intensity of fluorescent light that reemerges from said suspension in a first area of said suspension, wherein said first area is located close to a particle;
  (f) changing the thickness of said container in said first area by a known amount by pressing on said container from outside of said container and measuring a second intensity of fluorescent light that reemerges from said suspension in said first area;
  (g) measuring a third intensity of fluorescent light that reemerges from said suspension in a second area of said suspension, wherein said second area contains at least one particle; and
  (h) determining the volume of said at least one particle based on said fluorescence light intensity values and said known change in thickness of said container.

28. A method for determining the volume of particles in a liquid, the method comprising:
  (a) obtaining a suspension of particles in a liquid;
  (b) adding a fluorescent dye to said suspension forming a mixture, wherein said fluorescent dye does not substantially leak into said particles and is able to absorb excitation light at wavelengths that are only weakly absorbed by said particles and emit fluorescence light at wavelengths that are only weakly absorbed by said particles;
  (c) depositing said mixture into a container having at least one transparent window;
  (d) illuminating said mixture with light, whereby the wavelength of said light is selected so that the light is being absorbed by said dye but only weakly absorbed by said particles;
  (e) measuring a first intensity of fluorescent light that reemerges from said mixture in a first area of said mixture, wherein said first area is located close to a particle;
  (f) changing the thickness of said container in said first area by a known amount by pressing on said container from outside of said container and measuring a second intensity of fluorescent light that reemerges from said mixture in said first area;
  (g) measuring a third intensity of fluorescent light that reemerges from said mixture in a second area of said mixture, wherein said second area contains at least one particle; and
  (h) determining the volume of said at least one particle based on said fluorescence light intensity values and said known change in thickness of said container.

29. The method of claim 27 wherein the particle is a cell.
30. The method of claim 28 wherein the particle is a cell.
31. The method of claim 29 wherein the cell is a human cell.
32. The method of claim 30 wherein the cell is a human cell.
33. The method of claim 29 wherein the cell is a red blood cell.
34. The method of claim 30 wherein the cell is a red blood cell.
35. The method of claim 27 wherein the liquid is a biological or medical sample.
36. The method of claim 28 wherein the liquid is a biological or medical sample.
37. The method of claim 35 wherein the biological or medical sample comprises a body fluid.

38. The method of claim 36 wherein the biological or medical sample comprises a body fluid.

39. The method of claim 37 wherein the body fluid is selected from the group consisting of blood, urine, sputum, saliva and lymph fluid.

40. The method of claim 38 wherein the body fluid is selected from the group consisting of blood, urine, sputum, saliva and lymph fluid.

41. The method of claim 35 wherein the biological or medical sample comprises tissue culture cells.

42. The method of claim 36 wherein the biological or medical sample comprises tissue culture cells.

43. The method of claim 35 wherein the biological or medical sample comprises bacterial cells.

44. The method of claim 36 wherein the biological or medical sample comprises bacterial cells.

45. The method of claim 27 wherein the container is an optical cuvette.

46. The method of claim 28 wherein the container is an optical cuvette.

47. The method of claim 45 wherein the optical cuvette comprises at least one transparent window.

48. The method of claim 46 wherein the optical cuvette comprises at least one transparent window.

49. The method of claim 45 wherein the optical cuvette comprises a microscope slide and a cover slip.

50. The method of claim 46 wherein the optical cuvette comprises a microscope slide and a cover slip.

51. The method of claim 27 wherein the dye is selected from the group consisting of TO-PRO-3 and TO-PRO-5.

52. The method of claim 28 wherein the dye is selected from the group consisting of TO-PRO-3 and TO-PRO-5.

* * * * *